(12) United States Patent
Uribe et al.

(10) Patent No.: US 11,389,388 B2
(45) Date of Patent: Jul. 19, 2022

(54) LEAVE-ON HAIR STYLING COMPOSITIONS AND METHODS OF USE

(71) Applicant: L'OREAL, Paris (FR)

(72) Inventors: Santiago Uribe, Butler, NJ (US); Sana Ghani, Elizabeth, NJ (US); Azizah Khader Suleiman, Paterson, NJ (US); Anand Ramachandra Mahadeshwar, Scotch Plains, NJ (US); Vanessa Decarlo, Roselle Park, NJ (US)

(73) Assignee: L'OREAL, Paris (FR)

( * ) Notice: Subject to any disclaimer, the term of this patent is extended or adjusted under 35 U.S.C. 154(b) by 35 days.

(21) Appl. No.: 16/023,610

(22) Filed: Jun. 29, 2018

(65) Prior Publication Data

US 2020/0000701 A1 Jan. 2, 2020

(51) Int. Cl.
| | |
|---|---|
| *A61K 8/73* | (2006.01) |
| *A61K 8/34* | (2006.01) |
| *A61K 8/97* | (2017.01) |
| *A61Q 5/06* | (2006.01) |

(52) U.S. Cl.
CPC .............. *A61K 8/731* (2013.01); *A61K 8/345* (2013.01); *A61K 8/97* (2013.01); *A61Q 5/06* (2013.01); *A61K 2800/262* (2013.01); *A61K 2800/34* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 3,972,997 A * | 8/1976 | Nakashio | ............. A61K 8/0212 424/49 |
| 8,242,097 B2 | 8/2012 | Philippe | |
| 9,918,922 B1 | 3/2018 | Botto et al. | |
| 9,999,580 B2 | 6/2018 | Manning et al. | |
| 2001/0022967 A1 | 9/2001 | Brandt et al. | |
| 2003/0099692 A1 | 5/2003 | Lydzinski et al. | |
| 2005/0124798 A1 | 6/2005 | Quinn et al. | |
| 2006/0193789 A1 | 8/2006 | Tamarkin et al. | |
| 2007/0275927 A1 | 11/2007 | Philippe | |
| 2008/0071077 A1 * | 3/2008 | Dijk | ........................ A61K 8/731 536/56 |
| 2008/0124294 A1 | 5/2008 | Philippe | |
| 2008/0213199 A1 | 9/2008 | Philippe | |
| 2008/0260674 A1 | 10/2008 | Philippe | |
| 2009/0074697 A1 * | 3/2009 | Huynh | ..................... A61K 8/60 424/70.13 |
| 2010/0209377 A1 | 8/2010 | Drovetskaya et al. | |
| 2010/0247459 A1 | 9/2010 | Drovetskaya et al. | |
| 2010/0254932 A1 | 10/2010 | Benabdillah et al. | |

OTHER PUBLICATIONS

Bergfeld et al. "Microbial Polysaccharides", Scientific Literature Review, (Year: Nov. 29, 2011).*
Majewicz, "Cellulose Ethers", Encyclopedia of Polymer Science and Technology, Oct. 15, 2002 (Year: 2002).*
Mintel Database 1 results, 2018, pp. 1-101 http://www.gnpd.com.
Mintel Database 2 results, 2017, pp. 1-101 http://www.gnpd.com.
Mintel Database 3 results, 2015, pp. 1-118 http://www.gnpd.com.

* cited by examiner

*Primary Examiner* — Isis A Ghali
(74) *Attorney, Agent, or Firm* — Polsinelli PC

(57) ABSTRACT

The present disclosure relates to leave-on hair styling compositions, and to methods for styling hair using the compositions. The leave-on hair styling compositions include: (a) pullulan; (b) one or more cellulose ethers; (c) one or more water-soluble solvents; and (d) water. The leave-on hair styling compositions are unique in that they impart durable styling or shaping benefits, volume and fullness, smoothness, shine, texture, control fizziness, and provide overnight style, without the need for silicones and/or synthetic film forming polymers.

9 Claims, No Drawings

LEAVE-ON HAIR STYLING COMPOSITIONS AND METHODS OF USE

FIELD OF THE DISCLOSURE

The present disclosure relates to leave-on hair styling compositions and to methods for styling hair using the compositions. The leave-on hair styling compositions contain a combination of pullulan and cellulose ether(s), and are useful in a variety of methods for styling hair, for example, to provide smoothness, curl definition, shine, volume, hold, texture, and frizz control; and for providing overnight styling properties.

BACKGROUND

Consumers desire new multi-functional hair products that can impart good styling benefits to hair, are durable, and impart certain cosmetic characteristic to the hair. Such products should be pleasing to the senses, have innovative, interesting and/or pleasing textures, without loss in functional performance. Furthermore, many consumers prefer hair products that provide a light feel, are easy to apply, and add shine and luster to the hair.

Traditional hair products on the cosmetic market appear in various forms. They range anywhere from solutions, foams, gels, creams, waxes, mousses, sprays, serums, to aerosols and can impart a variety of levels of protection to the hair depending on the state of the hair and the components of the product. Generally, products that are designed to impart styling or shaping benefits to hair are in the form of hair styling or hair care/hair treatment products. Some of these products are often sticky or tacky upon application and once dry, may become stiff and/or "crunchy" (i.e. the film is hard and brittle resulting in a crunching feel or sound when the hair is touched), which is undesirable for many consumers.

Current products for imparting styling or shaping benefits to hair often include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film.

SUMMARY OF THE DISCLOSURE

The instant disclosure relates to compositions and methods for styling hair. The compositions and methods are unique in their ability to provide a variety of desirable properties to hair, for example, maintain a desired shape of hair, achieve long-lasting frizz control, provide strong styling hold, and impart a pleasant texture and body to the hair. Furthermore, upon application to the hair, the compositions have a clean, natural, and light-weight feel.

Traditionally, hair styling products required silicones and/or synthetic polymer to provide styling benefits such as those provided by the instant case. Silicones and/or synthetic polymers can provide slip, align the hair fibers (provide conditioning), improve texture, etc., but also tend to impart a "greasy" or "dirty" feeling to the hair. Additionally, their beneficial effects do not tend be long-lasting. The leave-on hair styling compositions of the instant disclosure provide the styling and sensory benefits mentioned above without the need for silicones and synthetic polymers. Furthermore, the styling and sensory benefits provided by the leave-on hair styling compositions of the instant case are extremely long lasting.

The leave-on hair styling compositions include:
(a) at least 2 to about 20 wt. % of pullulan;
(b) about 0.05 to about 10 wt. % of one or more cellulose ethers;
(c) about 0.1 to about 25 wt. % of one or more water-soluble solvents; and
(d) at least 50 wt. % of water;
wherein all weight percentages are based on the total weight of the leave-on hair styling composition.

Non-limiting examples of cellulose ethers include methyl cellulose, ethyl cellulose, propyl cellulose, methylethyl cellulose, carboxymethyl cellulose (cellulose gum), ethyl carboxymethyl cellulose, hydroxyethyl cellulose, hydroxypropyl cellulose, carboxymethyl hydroxyethyl cellulose, methyl hydroxyethyl cellulose, hydroxypropyl methyl cellulose, ethyl hydroxyethyl cellulose, methyl ethyl hydroxyethyl cellulose, and a mixture thereof.

Non-limiting example of useful water-soluble solvents include monomeric polyols, a glycol, glycerin, a polyhydric alcohol, and a mixture thereof. Exemplary monomeric polyols that may be included in the hair styling compositions include, but are not limited to, glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Additional non-limiting examples of polyols that have one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

The leave-on hair styling compositions can be in a variety of suitable forms. Suitable forms include, but are not limited to low to moderate viscosity liquids, lotions, milks, mousses, sprays, gels, creams, pastes, clays, bars, conditioners, and the like. In some cases, the leave-on hair styling composition is preferably not in the form of an emulsion. In some cases, the leave-on hair styling composition is free or essentially free of silicones and/or synthetic polymers including synthetic film forming polymers and/or pigments and/or surfactants. Moreover, in some instances, the leave-on hair styling composition is transparent or translucent.

The leave-on hair styling compositions may be used in various methods for treating/styling hair, for example, human hair, including human hair of an individual's head (which does not include the eyebrows and eyelashes). For example, the compositions are useful for: (i) improving or retaining curl definition of hair; (ii) imparting humidity resistance to hair; (iii) reducing hair frizz; (iv) controlling hair volume; (v) styling hair; (vi) straightening hair; and (vi) improving the appearance of hair. The methods include, for example, applying a leave-on hair treatment composition to the hair and, without removing the hair styling composition from the hair, manipulating the hair into a desired style.

DETAILED DESCRIPTION OF THE DISCLOSURE

The present disclosure relates to compositions and methods for treating and/or styling hair. The compositions remain on the hair after application and are therefore referred to as "leave-on" or "leave-in" hair styling composition. The leave-on hair styling compositions contain a combination of pullulan and cellulose ether(s), and are useful in methods for providing a variety of styling and sensory benefits to the hair. The leave-on hair styling compositions include:
  (a) at least 2 to about 20 wt. % of pullulan;
  (b) about 0.05 to about 10 wt. % of one or more cellulose ethers;
  (c) about 0.1 to about 25 wt. % of one or more water-soluble solvents;
  (d) at least 50 wt. % of water;
    wherein all weight percentages are based on the total weight of the leave-on hair styling composition.

The leave-on hair styling compositions impart durable styling or shaping benefits, volume and fullness, and control fizziness without the need for silicones and/or synthetic film forming polymers (although these components can optionally be included, if desired). Therefore, the leave-on hair styling composition may optionally be free or essentially free of silicones and/or synthetic film forming polymers.

As noted above, the amount of pullulan in the leave-on hair styling composition is typically at least 2 to about 20 wt. %, based on the total weight of the hair styling composition. In some cases, the total amount of pullulan in the hair styling composition is at least 2 to about 15 wt. %, at least 2 to about 12 wt. %, at least 2 to about 10 wt. %, at least 2 to about 8 wt. %, at least 3 to about 20 wt. %, at least 3 to about 15 wt. %, at least 3 to about 12 wt. %, at least 3 to about 10 wt. %, or at least 3 to about 8 wt. %, based on the total weight of the hair styling composition.

Cellulose ethers are polymers produced by the chemical modification of cellulose. Non-limiting examples of cellulose ethers include methyl cellulose, ethyl cellulose, propyl cellulose, methylethyl cellulose, carboxymethyl cellulose (cellulose gum), ethyl carboxymethyl cellulose, hydroxyethyl cellulose, hydroxypropyl cellulose, carboxymethyl hydroxyethyl cellulose, methyl hydroxyethyl cellulose, hydroxypropyl methyl cellulose, ethyl hydroxyethyl cellulose, methyl ethyl hydroxyethyl cellulose, and a mixture thereof. A particularly preferred cellulose ether is carboxymethyl cellulose (cellulose gum).

The total amount of cellulose ether(s) in the leave-on hair styling composition is typically about 0.05 to about 10 wt. %, based on the total weight of the hair styling composition. In some cases, the total amount of cellulose ether(s) in the leave-on hair styling composition is about 0.05 to about 8 wt. %, about 0.05 to about 6 wt. %, about 0.05 to about 5 wt. %, about 0.05 to about 3 wt. %, about 0.1 to about 10 wt. %, about 0.1 to about 8 wt. %, about 0.1 to about 6 wt. %, about 0.1 to about 5 wt. %, or about 0.1 to about 3 wt. %, based on the total weight of the hair styling composition.

As suggested by the ranges set forth above for pullulan and for the cellulose ether(s), it is possible (and in some cases preferable) for the amount of pullulan to be greater than the total amount of all cellulose ether(s) in the hair treatment composition. Accordingly, in some instances the ratio of the total amount of pullulan to the total amount of cellulose ether(s) is about 2:1 to about 30:1 (pullulan: cellulose ether(s)). In some instances, the ratio of pullulan to cellulose ether(s) is about 3:1 to about 30:1, about 5:1 to about 30:1, about 5:1 to about 25:1, about 10:1 to about 25:1, or about 15:1 to about 25:1. The amount of pullulan in the hair styling compositions, however, does not always exceed the amount of cellulose ether(s). Therefore, in some cases the ratio of the total amount of pullulan to the total amount of cellulose ether(s) is about 1:5 to about 5:1, about 1:3 to about 3:1, or about 1:2 to about 2:1.

The hair styling compositions include one or more water-soluble solvents, such as, for example, an organic solvent. The term "water-soluble solvent" denotes a compound that is liquid at room temperature and water-miscible (miscibility in water of greater than 50% by weight at 25° C. and atmospheric pressure).

Non-limiting examples of water-soluble solvents include lower monoalcohols and monomeric polyols. Non-limiting examples of lower monoalcohols are those containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

Non-limiting examples of water-soluble organic solvents that may be mentioned include linear or branched $C_2$-$C_4$ alkanols, such as ethanol and isopropanol; polyols and polyol ethers, for instance 2-butoxyethanol, glycerol, propylene glycol, dipropylene glycol, polyethylene glycols, propylene glycol monomethyl ether, diethylene glycol monomethyl ether and monoethyl ether, and also aromatic alcohols, for instance benzyl alcohol or phenoxyethanol, and mixtures thereof. In some cases, glycerol is a particularly preferred water soluble solvent.

In some cases, the one or more water-soluble solvents include one or more monomeric polyols. Non-limiting examples of monomeric polyols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, 1,6-hexanediol, 2-methyl-2,4-pentanediol, polyethylene glycol, 1,2,4-butanetriol, and 1,2,6-hexanetriol. Non-limiting examples of monomeric polyols having one or more aliphatic diols include 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and mixtures thereof.

The total amount of the one or more water-soluble solvents can vary but is typically about 0.1 to about 25 wt. %, based on the total weight of the leave-on hair styling composition. In some cases, the total amount of the water-soluble solvent(s) is about 0.1 to about 20 wt. %, about 0.1 to about 15 wt. %, about 0.1 to about 10 wt. %, about 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the hair styling composition.

The leave-on hair styling compositions include water, which is often the predominant ingredient in the hair styling compositions. Therefore, the hair styling compositions may be referred to as "aqueous leave-on hair styling compositions." The total amount of water can vary, but typically the total amount of water in the leave-on hair styling compositions is at least 50 wt. %, based on the total weight of the leave-on hair styling composition. In some cases, the total amount of water may be at least 60 wt. %, at least 65 wt. %, or at least 70 wt. %, based on the total weight of the hair styling composition. It is understood that the amount of water cannot exceed 100 wt. %, and does not reach 100 wt. %, due to the inclusion of other ingredients, for example, the pullulan, the cellulose ether(s), and the water soluble solvent(s). In some cases, the amount of water is at 70 wt % to about 95 wt %, at least 70 wt. % to about 92 wt. %, at least 75 wt. % to about 95 wt. %, at least 75 wt. % to about 92 wt. %, at least 80 wt. % to about 95 wt. %, at least 80 wt. % to about 92 wt. %, at least 85 wt. % to about 95 wt. %, at least 85 wt. % to about 92 wt. %, based on the total weight of the hair styling composition.

The hair styling composition may optionally include one or more vegetal extracts. The term vegetal extract encompasses vegetable extracts, fruit extracts, kelp extracts, algae extracts, and all types of plant extracts. Non-limiting examples of vegetal extracts include lyophilisates, evaporates, and/or distillates from yeast, brewer spent grain (by-product of beer brewing), barley, soybean, soybean milk, oat, lavender, licorice, ginger, *ginseng*, turmeric, apple, sea whip, algae, aloe vera (barbadensis), tea, chamomile, and birch tree. In some instances, the vegetal extract is a cactus or succulent extract, for example, from *Cereus Grandiflorus* cactus, from the Opuntia cactus, and/or from aloe vera (barbadensis). A particularly useful vegetal extract is aloe vera (barbadensis) leaf juice.

The total amount of vegetal extract in the hair styling compositions, if present, can vary but is typically about 0.01 to about 10 wt. %, based on the total weight of the hair styling composition. The total amount of vegetal extract can be about 0.01 to about 5 wt. %, about 0.01 to about 3 wt. %, about 0.05 to about 10 wt. %, about 0.05 to about 5 wt. %, or about 0.05 to about 3 wt. %, based on the total weight of the hair styling composition.

In some instances, the hair styling compositions of the present disclosure include at least one stabilizer and/or thickening agent, which is different than the pullulan and cellulose ethers already discussed and included in the leave-on hair styling composition. Nonetheless, in some instances it is preferable that the hair styling composition be free or essentially free of stabilizer(s) and/or thickening agent(s) other than the pullulan and cellulose ethers already discussed and included in the leave-on hair styling composition. Non-limiting examples of stabilizers and/or thickening agents include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sodium carboxymethyl dextran, sodium carrageenan, tragacanth gum, xanthan gum, biosacharide gum, and mixtures thereof.

The stabilizer and/or thickening agent(s) may be a thickening polymer. Non-limiting examples of thickening polymers include polyvinyl pyrrolidone, sodium alginate, xanthan gum, modified xanthan gum, tragacanth gum, guar gum, acacia gum, Arabic gum, polyacrylic acid, methylmethacrylate copolymer, carboxyvinyl polymer, dextrin, pectin, chitin, levan, elsinan, collagen, gelatin, zein, gluten, soy protein, casein, polyvinyl alcohol, carboxylated polyvinylalcohol, sulfonated polyvinyl alcohol, starch, starch derivatives, proteins, chitosan, chitosan derivatives, polyethylene glycol, tetramethylene ether glycol, and mixtures thereof.

The total amount of the stabilizer and/or thickening agent(s) if present, is about 0.01 to about 10 wt. %, based on the total weight of the leave-on hair styling composition. In some cases, the total amount of stabilizer and/or thickening agent(s) is about 0.01 to about 8 wt. %, about 0.01 to about 6 wt. %, about 0.01 to about 5 wt. %, about 0.05 to about 10 wt. %, about 0.05 to about 8 wt. %, about 0.05 to about 6 wt. %, about 0.05 to about 5 wt. %, or about 0.1 to about 10 wt. %, about 0.1 to about 8 wt. %, about 0.1 to about 6 wt. %, or about 0.1 to about 5 wt. %, based on the total weight of the hair styling composition.

In some instances, the hair styling compositions of the present disclosure may include at least one surfactant, such as one or more nonionic surfactant(s), anionic surfactant(s), cationic surfactant(s), and/or amphoteric/zwitterionic surfactant(s). Nonetheless, in some instances it is preferable that the hair styling composition be free or essentially free of surfactants. For instance, in one embodiment, the hair styling compositions are free or essentially free of nonionic surfactants and/or anionic surfactants and/or cationic surfactants, and/or amphoteric/zwitterionic surfactants. A non-limiting description of surfactants that may optionally be included (or excluded) from the hair styling composition is provided later, under the heading "Surfactants."

The total amount of the surfactant(s) in the hair styling composition, if present, may vary but may be about 0.01 to about 10 wt. %, based on the total weight of the leave-on hair styling composition. In some cases, the total amount of surfactant(s) in the hair styling composition, if present, is about 0.01 to about 8 wt. %, about 0.01 to about 6 wt. %, about 0.01 to about 5 wt. %, about 0.05 to about 10 wt. %, about 0.05 to about 8 wt. %, about 0.05 to about 6 wt. %, about 0.05 to about 5 wt. %, about 1 to about 10 wt. %, about 1 to about 8 wt. %, about 1 to about 6 wt. %, or about 1 to about 5 wt. %, based on the total weight of the hair styling composition.

The hair styling compositions of the instant disclosure are unique in that they do not require synthetic polymers such as synthetic film-forming polymers. In fact, the leave-on hair styling compositions do not necessarily require any synthetic ingredients. In some cases, synthetic film-forming polymer or synthetic polymer may be included but in other cases, they may be excluded. The term "synthetic polymer" (or "synthetic film-forming polymer") means a polymer, which is purely synthetic, or not of natural origin, especially those polymers, which are made by radical polymerization of ethylenically unsaturated monomers or by polycondensation. The term "natural polymer" means a polymer of natural origin, which includes those that have been subsequently chemically or physically modified (but retains at least 50% of its molecular structure from the original natural source). In particular, the term "natural original ingredient" refers to one of the following:

1. An ingredient which remains unchanged from its natural state; or
2. An ingredient which has undergone chemical or other processing which modifies it from its natural state but which retains at least 50% of its molecular structure from the original natural source.

In general, a naturally derived ingredient is processed to improve its stability, efficacy and/or safety for use in leave-on hair styling products. The degree of processing varies for each ingredient, but at the end only an ingredient that retains at least 50% of its molecular structure from the original natural source is considered natural origin. In some cases, the leave-on hair styling compositions of the instant disclosure are "natural leave-on hair styling compositions." A "natural leave-on hair styling composition" is a leave-on hair styling composition comprising only "natural original ingredients," as defined above.

Non-limiting examples of synthetic film-forming polymers (which in some cases may be included or excluded from the instant leave-on hair styling compositions) include non-ionic hair-fixing polymers (e.g., copolymerizates of vinyl pyrrolidone and vinyl acetate, terpolymers of vinyl pyrrolidone, vinyl acetate and vinyl propionate, polyacrylamides, polyvinyl alcohols and polyethylene glycol/polypropylene glycol copolymers. Polyvinyl pyrrolidone, polyvinyl caprolactam and their copolymers with at least one further nonionic monomer, for example, polyvinylpyrrolidone/vinyl acetate copolymers) and anionic hair-fixing polymers such as synthetic homo- or copolymers with neutralizable monomer units containing acid groups, which are copolymerizable with comonomers, if necessary, which contain no acid groups. The acid groups may include —COOH, —SO$_3$H, —OSO$_3$H, —OPO$_2$H, —PO$_3$H$_2$. The acid groups can be unneutralized, or partially or completely neutralized.

Furthermore, as already mentioned, the leave-in hair styling compositions do not require silicones (silicone and silicone containing materials). Non-limiting examples of silicones (which may optionally be included or excluded from the instant leave-on hair styling compositions) include dimethicone, dimethiconol, amodimethicone, cyclomethicones, amino-modified silicones, and polyether-modified silicones.

In some instances, the leave-in hair styling compositions do not require alcohols, in particular, monohdyric alcohols. Non-limiting examples of monohydric alcohols include lower monohydric alcohols having 8 carbons or less, having 6 carbons or less, or having 4 carbons or less. Thus, the hair styling compositions may optionally be free or essentially free of alcohols, in particular, monohydric alcohols.

Similarly, in some instances, the leave-in hair styling compositions do not require pigments, especially pigments that impart a coloring effect on hair. The hair styling compositions impart a natural look to the hair and therefore do not need to color the hair. Accordingly, the hair styling compositions are typically free or essentially free of pigments that color or alter the appearance of hair. Nonetheless, small amounts of colorants may be included in the hair styling compositions in order to provide an aesthetic look to the product itself. Such colorants modify the color or look of the product but do not modify the color or look of the hair (onto which the product is applied for styling) to the naked eye. The difference between a pigment included in a hair styling composition for altering the color or look of the hair and a colorant included in a product for altering the color or look of the product (without altering the color or look of the hair to the naked eye), is well understood by those working in the development and manufacture of cosmetics.

In some cases, the hair styling composition may be transparent or translucent. The term "translucent" as used herein with respect to a translucent composition means that the composition permits the passage of light but does not necessarily allow for detailed objects to be distinguished. The term "transparent" with respect to a transparent composition, however, means that the composition permits the passage of light and also makes possible the distinguishing of objects. In other words, a transparent composition is clearer than a translucent composition. Colorants can be included in a translucent or transparent composition without destroying the translucent or transparent characteristics of the composition. In other words, the terms do not necessarily require compositions to be color-free like pure water, but include colored products that appear, for example, like colored glass. The term "transparent" with respect to compositions of the instant disclosure indicates that the composition has transmittance of at least 80% at a wavelength of 600 nm, for example measured using a Lambda 40 UV-visible spectrometer, at a concentration of 0.5% by weight in water. The compositions may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure.

In one embodiment, the leave-on hair styling compositions of the instant disclosure include:
(a) at least 2 to about 20 wt. %, preferably at least 2 to about 15 wt. %, more preferably at least 3 to about 10 wt. % of pullulan;
(b) about 0.05 to about 10 wt. %, preferably about 0.05 to about 8 wt. %, more preferably about 0.1 to about 6 wt. % of one or more cellulose ethers, preferably cellulose gum;
(c) about 0.1 to about 25 wt. %, preferably about 0.1 to about 15 wt. %, more preferably about 1 to about 10 wt. % of one or more water-soluble solvents, for example, glycerin, mono-alcohols, polyols (polyhydric alcohols), glycols, and a mixture thereof, preferably glycerin;
(d) at least 50 wt. %, preferably at least 60 wt. %, more preferably at least 65 to about 95 wt. % of water;
(e) optionally, about 0.01 to about 10 wt. %, preferably about 0.01 to about 5 wt. %, more preferably about 0.05 to about 5 wt. % of one or more vegetal extracts, preferably aloe vera leaf juice; and
(f) optionally, one or more preservatives;
wherein all weight percentages are based on the total weight of the leave-on hair styling composition;
the composition is not an emulsion; and
the composition is essentially free of silicones and synthetic film forming polymers.

The leave-on hair styling compositions of the above-embodiment can include or exclude the various additional components discussed throughout the instant disclosure. For example, the hair styling composition may be free or essentially free of pigments. Similarly, the hair styling composition may be transparent or translucent. In some instances, the only thickening agents in the hair styling composition are the pullulan and the cellulose ether(s).

In another embodiment, the leave-on hair styling compositions of the instant disclosure include:
(a) at least 2 to about 20 wt. %, preferably at least 2 to about 15 wt. %, more preferably at least 3 to about 10 wt. % of pullulan;
(b) about 0.05 to about 10 wt. %, preferably about 0.05 to about 8 wt. %, more preferably about 0.1 to about 6 wt. % of cellulose gum;
(c) about 0.1 to about 25 wt. %, preferably about 0.1 to about 15 wt. % of glycerin;
(d) at least 50 wt. %, preferably at least 60 wt. %, more preferably at least 65 to about 95 wt. % of water;
(e) optionally, about 0.01 to about 10 wt. %, preferably about 0.01 to about 5 wt. %, more preferably about 0.05 to about 5 wt. % of one or more vegetal extracts, preferably aloe vera leaf juice; and
(f) optionally, one or more preservatives;
wherein all weight percentages are based on the total weight of the leave-on hair styling composition;
the composition is not an emulsion; and
the composition is essentially free of pigments and silicones.

The leave-on hair styling compositions of the above-embodiment can include or exclude the various additional components discussed throughout the instant disclosure. For example, the hair styling composition may be free or essentially free of synthetic film forming polymers. Similarly, the hair styling composition may be transparent or translucent.

In some instances, the only thickening agents in the hair styling composition are the pullulan and the cellulose ether(s).

All of the leave-on hair styling compositions described throughout the disclosure (including the embodiments above) may optionally be free or essentially free of synthetic ingredients, for example, synthetic film-forming polymers. Similarly, all of the leave-on hair styling compositions described throughout the disclosure may be free or essentially free of silicones. Additionally, all of the leave-on hair styling compositions described throughout the disclosure may be free or essentially free of lower monohydric alcohols having 8 carbons or less. All of the leave-on hair styling compositions described throughout the disclosure may be free or essentially free of pigments.

The leave-on hair styling compositions described throughout the instant disclosure may be in any suitable physical form. Suitable forms include, but are not limited to low to moderate viscosity liquids, lotions, milks, mousses, sprays, gels, creams, pastes, clays, bars, conditioners, and the like. In some cases, the leave-on hair styling composition is in the form of a liquid product with a water-like consistency.

Regardless of the form of the leave-on hair styling composition, in this case, the leave-on hair styling compositions are typically not emulsions, i.e., the leave-on hair styling compositions are not an oil-in-water emulsions, water-in-oil emulsions, silicone-in-water emulsions, or water-in-silicone emulsions. Accordingly, the leave-on hair styling compositions do not require emulsifiers and therefore may be free or essentially free of emulsifiers.

As suggested by the term "leave-on hair styling compositions," these compositions are formulated so that they can remain on the hair for extended periods of time, i.e., the compositions are applied to the hair, for example, during styling of the hair and allowed to remain for one or more hours, or one or more days before being removed, for example, by washing. In other words, the leave-on hair styling compositions are applied to the hair and allowed to remain on the hair without immediate rinsing or removal. The leave-on hair styling compositions may be applied to the hair, for example, after shampooing, before or during the styling process. The hair may be wet, damp, or already dry when the hair styling composition is applied to the hair. In some cases, the leave-on hair styling composition may be applied to wet or damp hair after which the hair is air dried or blow dried and styled. In other cases, the hair may be previously dried and the leave-on hair styling composition is applied to dry hair, in order to treat, shape, or style the hair.

Due to the durability and natural look and feel of the hair styling compositions, in some cases, the compositions may remain on the hair overnight. For example, the compositions may be allowed to remain on the hair overnight and not removed the next morning. During the next morning, the hair is simply re-styled as desired or needed. Due to the durability and lastingness of the hair styling composition, the hair retains its style/shape for long periods of time. Unlike other products (e.g., hair sprays, typical gels, etc.), the hair styling compositions do not flake off (dust off) or otherwise lose their styling properties.

The leave-on hair styling compositions may be packaged in a variety of different containers, such as, for example, a ready-to-use container. Non-limiting examples of useful packaging include tubes, jars, caps, unit dose packages, and bottles, including squeezable tubes and bottles.

The leave-on hair styling compositions may be used in various methods for treating hair, specifically, human hair on an individual's head. For purposes of the instant disclosure, human hair on an individual's head refers to the hair on the top of an individual's head and not to the hair of eyebrows and eyelashes. In other words, the methods described throughout the instant disclosure relate to treating and styling the hair on the top of the head and not necessarily to treating and styling the eyebrows and eyelashes.

For example, the compositions are useful for: (i) improving or retaining curl definition of hair; (ii) imparting humidity resistance to hair; (iii) reducing hair frizz; (iv) controlling hair volume; (v) styling hair; (vi) straightening hair; and (vi) improving the appearance of hair; wherein the methods typically comprise applying a hair styling composition disclosed herein to the hair. These methods are particularly useful for average to fine hair. The hair styling compositions are useful in methods for imparting durable styling or shaping properties and/or frizz control to hair. The methods may include applying the leave-on hair styling composition to the hair, subsequently styling the hair while allowing the leave-on hair styling composition to remain on the hair, for example, for one or more hours, or one or more days before being removed by a subsequent washing. The leave-on hair styling composition may be applied to wet, damp, or already dry hair and can be air dried or blow dried. Application to wet hair that is allowed to air dry provides improvements in curl definition. If the hair is blow dried, the hair exhibits improved smoothness and discipline.

More exhaustive but non-limiting lists of components useful in the hair styling compositions disclosed herein are presented below.

Surfactants

Cationic Surfactants

The term "cationic surfactant" means a surfactant that is positively charged when it is contained in the composition according to the disclosure. This surfactant may bear one or more positive permanent charges or may contain one or more functions that are cationizable in the composition according to the disclosure.

Non-limiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

Anionic Surfactants

The term "anionic surfactant" means a surfactant comprising, as ionic or ionizable groups, only anionic groups. These anionic groups are chosen preferably from the groups $CO_2H$, $CO_2$, $SO_3H$, $SO_3$, $OSO_3H$, $OSO_3^-$, $O_2PO_2H$, $O_2PO_2H$ and $O_2PO_2^{2-}$.

The anionic surfactant(s) that may be used may be alkyl sulfates, alkyl ether sulfates, alkylamido ether sulfates, alkylaryl polyether sulfates, monoglyceride sulfates, alkylsulfonates, alkylamide sulfonates, alkylarylsulfonates, alpha-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group. Some of these compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfo succinates.

When the anionic surfactant(s) are in salt form, they may be chosen especially from alkali metal salts such as the sodium or potassium salt and preferably the sodium salt, ammonium salts, amine salts and in particular amino alcohol salts, or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts may be used.

Mention is also made of ($C_6$-$C_{24}$)alkyl sulfates, ($C_6$-$C_{24}$) alkyl ether sulfates, which are optionally ethoxylated, comprising from 2 to 50 ethylene oxide units, and mixtures thereof, in particular in the form of alkali metal salts or alkaline-earth metal salts, ammonium salts or amino alcohol salts. In some cases, the anionic surfactant(s) are chosen from ($C_{10}$-$C_{20}$)alkyl ether sulfates, and in particular sodium lauryl ether sulfate containing 2.2 mol of ethylene oxide.

Amphoteric Surfactants

Amphoteric surfactants useful in the cosmetic compositions disclosed herein may be chosen from betaines, sultaines, amphoacetates, amphoprionates, and mixtures thereof. More typically, betaines and amphoprionates are used, and most typically betaines. Betaines which can be used in the current compositions include those having the formulas below:

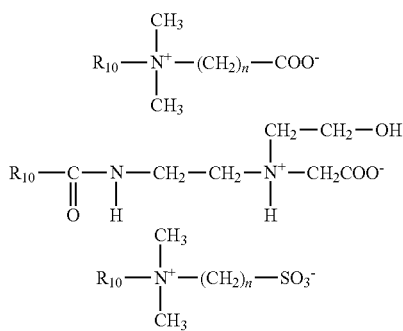

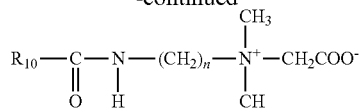

wherein $R^{10}$ is an alkyl group having 8-18 carbon atoms; and
n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

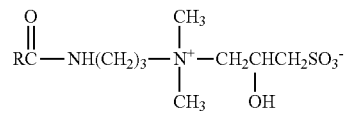

wherein

R is an alkyl group having 8-18 carbon atoms.

Useful alkylamphoacetates include those having the formula

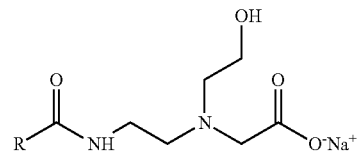

wherein

R is an alkyl group having 8-18 carbon atoms.

useful alkyl amphodiacetates include those having the formula

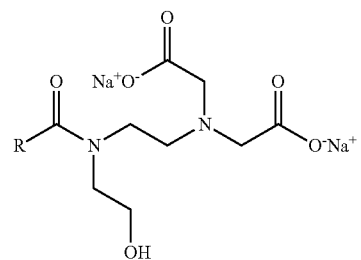

wherein

R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEG1 N by Goldschmidt (CTFA name: glyceryl stearate SE), can also be used.

Cationic Conditioning Agents

The cationic conditioning agents that may be employed in the compositions of the present disclosure can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic polymers. The term "cationic polymer" means any polymer comprising at least one cationic group and/or at least one group that may be ionized into a cationic group.

Particularly useful cationic polymers in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, and guar hydroxypropyltrimonium chloride.

Particularly preferred cationic polymers of the present invention include POLYMER JR-125, POLYMER JR-400, Polymer JR-30M hydroxyethyl cellulosic polymers (polyquaternium 10) available from AMERCHOL; JAGUAR C® 13-S, guar hydroxypropyltrimonium chloride, available from Rhodia; and MERQUAT® 100 and 280, a dimethyl dialkyl ammonium chloride (polyquaternium 6) available from Nalco.

The cationic polymer is generally present in an amount of from greater than 0% to about 15%, preferably from about 0.5% to about 10% by weight, and more preferably from about 1% to about 5% by weight, based on the total weight of the composition.

Cationic polymers useful herein include polyquaternium 4, polyquaternium 6, polyquaternium 7, polyquaternium 10, polyquaternium 11, polyquaternium 16, polyquaternium 22, and polyquaternium 32. Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125, POLYMER JR-400, Polymer JR-30M hydroxyethyl cellulosic polymers (polyquaternium 10) available from AMERCHOL; JAGUAR C13-S, guar hydroxypropyltrimonium chloride, available from Rhodia; and MERQUAT 100 and 280, a dimethyl dialkyl ammonium chloride (polyquaternium 6) available from Nalco.

Oils

The hair styling composition may optionally include (or optionally exclude) one or more oils, for example, silicone oils, fluoro oils, hydrocarbon-based oils, etc. The hair styling compositions are typically not an emulsion and therefore do not typically include large amounts of oils; and often do not include any oils. In other words, the hair styling compositions of the instant disclosure may be free or essentially free of oils. The term "oil" means any fatty substance which is in liquid form at room temperature (20-25° C.) and at atmospheric pressure (760 mmHg). The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa ($10^{-3}$ to 300 mmHg). The term "non-volatile oil" relates to oil which remains on the skin or the keratin fiber, at room temperature and atmospheric pressure, for at least several hours and which in particular has a vapor pressure of less than $10^{-3}$ mmHg (0.13 Pa).

The term "silicone oil" relates to oil comprising at least one silicon atom, and especially at least one Si—O group. The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Silicone Oils

As already mentioned, the hair styling compositions of the instant disclosure do not require silicone including silicone oils, and in many instances silicones and silicone oils are preferably excluded from the hair styling compositions. Nonetheless, there may be instances in which a silicone including a silicone oil may be desired. Non-limiting examples of silicone oils include dimethicone, cyclomethicone, polysilicone-11, phenyl trimethicone, trimethylsilylamodimethicone, and stearoxytrimethylsilane. In some cases, the cosmetic composition includes dimethicone, and optionally additional oils, including additional silicone oils. Typically, the one or more silicone oils is a non-volatile silicon oil. In some embodiments, the silicone oil is polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl (methyldiphenyl)trisiloxanes or (2-phenylethyl)trimethylsiloxysilicates.

Other examples of silicone oils that may be mentioned include volatile linear or cyclic silicone oils, especially those with a viscosity 8 centistokes ($8\times10^6$ $m^2/s$) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Fluoro Oils

The cosmetic compositions described herein may comprise one or more fluoro oils. For example, the onee or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The cosmetic compositions described herein may comprise one or more hydrocarbon-based oils. For example, the hydrocarbon-based oil may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, *quinoa* oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 40 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

(viii) fatty amides, such as isopropyl N-lauroyl sarcosinate, such as the product sold under the trade name Eldew SL 205® from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4, 6-pentamethylheptane), isodecane or isohexadecane, the oils sold under the Isopar or Permethyl trade names, branched C $C_8$-$C_{16}$ esters, and isohexyl neopentanoate.

The total amount of oil(s) in the hair styling composition, if present, can vary, but is typically about 0.01 to about 20 wt. %, based on the total weight of the hair styling composition. In some cases, the total amount of oil(s), if present, is about 0.01 to about 15 wt. %, about 0.01 to about 10 wt. %, about 0.01 to about 5 wt. %, about 0.1 to about 20 wt. %, about 0.1 to about 10 wt. %, about 0.1 to about 5 wt. %, or about 0.5 to about 5 wt. %, based on the total weight of the hair styling composition.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair styling compositions depending on the specific combination of other components, the form of the compositions, and/or the use of the formulation (e.g., hair spray, cream, paste, conditioner, etc.).

Implementation of the present disclosure is provided by way of the following examples. The examples serve to illustrate the technology without being limiting in nature.

Example 1

Hair Styling Composition

| | INCI US Name | A wt. % |
|---|---|---|
| Pullulan | PULLULAN | 4 |
| Carboxymethylcellulose | CELLULOSE GUM | 0.2 |
| Water-Soluble Solvent | GLYCERIN | 3 |
| Vegetal Extract | ALOE BARBADENSIS LEAF JUICE | 0.1 |
| Preservatives | SODIUM BENZOATE, SALICYLIC ACID, AND/OR POTASSIUM SORBATE | ≤2 |
| Miscellaneous | FRAGRANCE, pH ADJUSTERS, SALTS, ETC. | ≤3 |
| Water | WATER | QS 100% |

Example 2

Contribution of Main Components

The individual influence of pullulan and the cellulose ether in the hair styling composition of Example 1 was investigated. Compositions comprising only one of these two components were prepared and applied to mannequin heads and/or hair swatches. The effects were evaluated by experts. The compositions comprising only one of pullulan and a cellulose ether (cellulose gum) were identical to the composition of Example 1 except that only one of pullulan and cellulose gum was included. This was done to understand individual benefit of each ingredient and the combined benefit of the two ingredients. The results of the testing are presented in Table 1.

TABLE 1

| Raw Material Tested | Hair Styling Benefits | | | | | | | |
|---|---|---|---|---|---|---|---|---|
|  | Smoothness | Curl Definition | Shine | Discipline | Volume | Frizz Control | Hold | Texture |
| Pullulan | ✓ |  | ✓ |  |  |  |  |  |
| Cellulose Gum |  |  |  | ✓ |  |  | ✓ | ✓ |
| Pullulan & Cellulose Gum | ✓ | ✓ | ✓ | ✓ | ✓ | ✓ | ✓ | ✓ |

✓ indicates that the benefit reached an acceptable level.

The inclusion of pullulan in the hair styling composition resulted in a product that imparts appreciable smoothness and shine to the hair. The use of cellulose gum in the hair styling composition resulted in a product that provided discipline, hold, and texture to the hair. When used in combination, however, the product provided smoothness, curl definition, shine, discipline, volume, frizz control, hold, and texture to the hair. Of particular significance is the finding that the combination of pullulan and cellulose gum resulted in a product providing appreciable curl definition, volume, and frizz control even though neither pullulan nor cellulose gum alone provided these benefits. The data show a surprising synergistic interaction between the pullulan and the cellulose gum.

Other polymers and gums (dehydroxyxanthan gum and carrageenan) were combined with pullulan and compared with the results obtained with the combination of pullulan and cellulose gum. The compositions were identical to the composition of Example 1 except that the cellulose gum was replaced with dehydroxyxanthan gum or carrageenan and were tested as described above. The results of the testing are presented in Table 2.

Pullulan in combination with dehydroxyxanthan gum provided smoothness, hold/discipline, frizz control, volume, shaping, and sealed ends. However, this combination did not provide adequate shine and viscosity. Pullulan in combination with carrageenan provided shine, hold/discipline, frizz control, and shaping but did not provide adequate smoothness, volume, and viscosity. Pullulan in combination with cellulose gum provided all the desired attributes.

The foregoing description illustrates and describes the inventions. Additionally, the disclosure shows and describes only the preferred embodiments but it is to be understood that it is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" are used in their open, non-limiting sense.

All percentages, parts and ratios herein are based upon the total weight of the compositions of the present disclosure, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, less than about 0.05 wt. %, or

TABLE 2

| Raw Material Tested | Hair Styling Benefits | | | | | | | |
|---|---|---|---|---|---|---|---|---|
|  | Smoothness | Shine | Hold/ Discipline | Frizz Control | Volume | Shaping | Sealed Ends | Viscosity |
| Pullulan & Dehydroxyxanthan gum | ✓ |  | ✓ | ✓ | ✓ | ✓ | ✓ |  |
| Pullulan & Carrageenan |  | ✓ | ✓ | ✓ |  | ✓ |  |  |
| Pullulan & Cellulose Gum | ✓ | ✓ | ✓ | ✓ | ✓ | ✓ | ✓ | ✓ | none of the specified material. The components described for optional inclusion in the compositions of the disclosure may be free of the component(s) or may be "substantially free" or "essentially free" of the component(s).

The term "treat" (and its grammatical variations) as used herein refers to the application of the cosmetic compositions of the present disclosure onto the surface of the body, and in particular the skin and/or hair of the body.

The term "volatile", as used herein, means having a flash point of less than about 100° C.

The term "non-volatile", as used herein, means having a flash point of greater than about 100° C.

The term "substituted," as used herein, means comprising one or more substituents. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

The term "polymers," as defined herein, include homopolymers and includes copolymers formed from at least two different types of monomers.

The methods and compositions of the present disclosure can comprise, consist of, or consist essentially of the essential elements and limitations of the disclosure described herein, as well as any additional or optional ingredients, components, or limitations described herein or otherwise useful. Additionally, any component that is positively set forth in the present disclosure can be negatively excluded from the methods and compositions of the present disclosure, and in particular from the claims of the present disclosure. In particular, the methods and compositions of the present disclosure can be free or essentially free of any component that is positively set forth in the present disclosure.

Other than in the operating examples, or where otherwise indicated, all numbers expressing quantities of ingredients and/or reaction conditions can be modified, if desired, with the term "about," meaning within +/−5% of the indicated number.

The terms "a," "an," and "the" are understood to encompass the plural as well as the singular. Thus, the term "a mixture thereof" is synonymous with "mixtures thereof." Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

Some of the various categories of components identified may overlap. In such cases where overlap may exist and the composition includes both components (or the composition includes more than two components that overlap), an overlapping compound does not represent more than one component. For example, a fatty acid may be characterized as both a nonionic surfactant and a fatty compound. If a particular method or composition includes both a nonionic surfactant and a fatty compound, a single fatty acid will serve as only the nonionic surfactant or as only the fatty compound (the single fatty acid does not serve as both the nonionic surfactant and the fatty compound).

All publications, patents, and patent applications cited in the present disclosure are herein incorporated by reference, and for any and all purposes, as if each individual publication, patent, or patent application were specifically and individually indicated to be incorporated by reference. In the event of an inconsistency between the present disclosure and any publications, patents, or patent applications incorporated herein by reference, the present disclosure controls.

The invention claimed is:

1. A method for styling hair comprising:
   (i) applying to the hair a leave-on hair styling composition comprising:
      (a) at least 2 to about 20 wt. % of pullulan;
      (b) about 0.1 to about 5 wt. % of carboxymethyl cellulose (cellulose gum);
         wherein the weight ratio of (a) to (b) is from 5:1 to 30:1;
      (c) about 0.1 to about 25 wt. % of one or more water-soluble solvents; and
      (d) at least 50 wt. % of water;
         wherein all weight percentages are based on the total weight of the leave-on hair styling composition; and
   (ii) without rinsing the leave-on hair styling composition from the hair, manipulating the hair into a desired style.

2. A method for styling hair comprising:
   (i) applying to the hair a leave-on hair styling composition comprising:
      (a) at least 2 to about 15 wt. % of pullulan;
      (b) about 0.1 to about 3 wt. % of carboxymethyl cellulose (cellulose gum);
         wherein the weight ratio of (a) to (b) is from 10:1 to 30:1;
      (c) about 0.1 to about 25 wt. % of glycerin; and
      (d) at least 70 wt. % of water;
      (e) optionally, one or more vegetal extracts;
         wherein all weight percentages are based on the total weight of the leave-on hair styling composition,
         the leave-on hair styling composition is transparent, and
         the leave-on hair styling composition is not an emulsion;
   (ii) without rinsing the leave-on hair styling composition from the hair, manipulating the hair into a desired style.

3. The method of claim 2, wherein the leave-on hair styling composition is free of surfactants, emulsifiers, and monohydric alcohols.

4. The method of claim 1, wherein the one or more water-soluble solvents comprises glycerin.

5. The method of claim 1, wherein the leave-on hair styling composition is transparent.

6. The method of claim 1, wherein the leave-on hair styling composition is not an emulsion.

7. The method of claim 1, wherein the leave-on hair styling composition is free of surfactants, emulsifiers, and monohydric alcohols.

8. The method of claim 1, wherein the leave-on hair styling composition further comprises one or more vegetal extracts.

9. The method of claim 1, wherein the leave-on hair styling composition does not contain any polysaccharides other than the pullulan and the cellulose ether(s).

* * * * *